US006909914B2

(12) United States Patent
Pedrizzetti et al.

(10) Patent No.: US 6,909,914 B2
(45) Date of Patent: Jun. 21, 2005

(54) METHOD FOR GENERATING TIME INDEPENDENT IMAGES OF MOVING OBJECTS

(75) Inventors: Gianni Pedrizzetti, Prato (IT); Giovanni Tonti, Sulmona (IT); Emidio Marchese, Popoli (IT)

(73) Assignees: Esaote, S.p.A., Casale Monferrato (IT); AMID Srl, Rome (IT)

( * ) Notice: Subject to any disclaimer, the term of this patent is extended or adjusted under 35 U.S.C. 154(b) by 0 days.

(21) Appl. No.: 10/461,120

(22) Filed: Jun. 13, 2003

(65) Prior Publication Data

US 2004/0254440 A1 Dec. 16, 2004

(51) Int. Cl.$^7$ ................................................ A61B 5/05
(52) U.S. Cl. ................. 600/407; 600/410; 600/416; 600/425; 600/436; 600/437; 382/162; 382/254; 382/255; 382/260; 382/276; 128/923; 128/925; 250/455; 348/453

(58) Field of Search ............................. 600/407–482; 382/162, 254, 255, 260–308; 128/920–925; 250/455; 348/453

(56) References Cited

U.S. PATENT DOCUMENTS 6,106,466 A * 8/2000 Sheehan et al. ............. 600/443
6,396,961 B1 * 5/2002 Wixson et al. .............. 382/294

* cited by examiner

*Primary Examiner*—Brian L. Casler
*Assistant Examiner*—William Jung
(74) *Attorney, Agent, or Firm*—Woodard, Emhardt, Moriarty, McNett & Henry LLP

(57) ABSTRACT

A method for generating time independent images of moving objects with the image information being related to properties of the moving objects represented by sequences of digital images. The images are transformed into a series of space-time representations of the image data. A function is derived from the space-time representation images that approximates the object motion and is used to create time independent images of the moving objects.

36 Claims, 6 Drawing Sheets

METHOD FOR GENERATING TIME INDEPENDENT IMAGES OF MOVING OBJECTS

BACKGROUND OF THE INVENTION

The present invention relates to a method for generating time independent images of moving objects where the image information is related to properties of the moving object represented by parametric values.

In many practical, clinical, and industrial applications, the evaluation of properties in relation to a specific element of a system and the quantification of the variation of such properties with time is required. Methods are known for tracking the moving vascular wall (e.g. myocardium) from cardiovascular images in such a way as to extract from the image the properties (velocity, brightness, etc.) evaluated in relation to the tissue.

One driving example is the analysis of the time-course of blood flow in the capillary bed of the myocardium, based on echo-contrast imaging. The health of the myocardium can be established, among other ways, from the ability of the blood to reach all muscular cells; if a myocardial region is not perfused, then mechanical failure may occur (e.g. during angina or myocardial infarction). Therefore, it has been considered important to evaluate the perfusion properties of the different tissue regions. The quantification of myocardial perfusion is made by introducing a contrast agent in a vein, which moves with the blood. Quantification of its presence in the myocardial tissue is equivalent to quantification of myocardial perfusion (Becher and Burns, 2000). The analysis is made utilizing the ability of ultrasound machines to detect the echo enhancement deriving from a contrast medium that perfuses the myocardium. Recent examples of quantitative analysis of segmental perfusion are reported in literature (Mor-Avi et al., 1993; Wei et al., 1998; Masugata et al., 2001).

Crucial for an adequate quantification of the contrast signal is the ability to follow the systolic and diastolic movement of the heart walls. With respect to an ultrasound probe, the heart shows not only inherent movement but also displacements due to respiration. Moreover, the physician performing the examination can move the probe itself during the acquisition of the data. For these reasons, by trying to register the signal of the heart wall utilizing a region of interest (ROI) placed at a fixed location, the ROI frequently falls on other structures (such as the left or the right ventricular cavities or outside the heart). For these reasons, only if the heart wall is continuously tracked it is possible to extract the signal originating from the tissue and not outside of it and so to extract quantitative parameters of regional perfusion.

Such an approach has a widespread application—not only in echocardiography ((e.g., perfusion study analysis, regional wall velocity analysis and quantification, and computation of segmental strain and strain rate (Heimdal et al., 1998; Voigt et al., 2000)) but also in industrial applications when the tracking of a moving material is necessary, and in applications of visual recognition by intelligent electronic devices.

According to a first-known method, the quantification of wall-related properties is performed simply by analyzing the properties within an ROI (sometimes just a few pixels within the image), selected well inside the myocardial tissue. It is then important to verify that the selected ROI remains inside the tissue in all the images of the sequence; otherwise, information that does not pertain to the tissue may be included and the analysis may be corrupted. To make sure that erroneous samples are not introduced into the dataset, the sequence has to be reviewed frame by frame; when the ROI falls outside the tissue, it must be moved manually on the wall. It is evident how such an approach is inherently extremely time-consuming (in most cases, for each ROI more than 100 frames must be reviewed, and a compete evaluation requires an analysis of up to 20 different ROIs). Sometimes this procedure can be performed automatically with methods that depend from the software available. In most cases, these methods are based on standard edge detection algorithms or on cross-correlation alignment methods (Pratt, 1991); however, these techniques do not guarantee the accuracy of the results which must still be verified manually because they incorporate no information about the structure and the geometry of the object that is recognized.

In another method, the brightness of an echographic image is evaluated along pixels that are aligned on an ideal segment crossing the moving object; for example, crossing the myocardium and having an origin and an end outside the myocardium. This is done for several successive images so that the variation with time of the brightness of each pixel along the ideal segment can be simultaneously represented for all times in a two-dimensional representation where one axis is the distance along the segment and the other axis is the time. The brightness of a point defined by a particular distance-time coordinate corresponds to the brightness of the pixel residing at the corresponding position in the original image.

This solution allows for easier automatic tracking of the movement and deformation of the tissue of the myocardium, such as its center and thickness, and to errors in the position of the relevant pixel or group of pixels.

This method also gives the possibility to calculate, after wall motion compensation, for each pixel a time evolution of the perfusion. To this extent, N transmural segments are used to define a tissue region, N digital images (M-mode-like) are achieved, and the brightness of the pixels or the group of pixels along the said region passing through the wall of the myocardium is represented in relation to the time at which the relative image has been taken.

By choosing an appropriate sequence or loop of echographic images to be recorded, it is thus possible to show the evolution of a physical process like the tissue dynamics during a heartbeat or, using a contrast agent, the perfusion process of the organ during contrast vein infusion.

Particularly relating to the example pertaining to the perfusion, a certain number of frames are extracted as representing a certain number of digital images from a echo-contrast recording during myocardial perfusion. The perfusion of a tissue region is evaluated by the time-evolution (growth) of brightness in a region of interest, like a single pixel or a group of pixels.

A so-called perfusion curve is then used to represent the variation of the brightness of the pixel or group of pixels with time. In order to obtain valuable and comparable numeric data, an appropriate parametric curve is fitted to the measured data to obtain corresponding perfusion parameters. Actually, the parameters of the best approximation with a standard curve are taken as the perfusion parameters. A standard function given in the literature for myocardial perfusion is the following exponential function $y(t)=A(1-e^{-Bt})$, where the two parameters A and B are the perfusion parameters. These two parameters contain synthetic information of the regional perfusion properties; two different measures can be compared by simply comparing the corresponding parameters. A quantification of echographic loops can be performed by extracting objective parameters from a region that can be quantitatively compared with the same parameters obtained in another region, in another patient, or in the same patient at different times. This so-called perfusion analysis is done differently in different applications.

Echography produces images of the relevant region in which the data of the reflected beam is not the pixel brightness itself. It is a graphical representation of a physical property of the organ under observation, like the reflectivity of the tissue, or, when using a contrast agent, the density of contrast bubbles, or the Doppler effects on the ultrasound echoes which gives information about the blood or tissue speed.

It appears clearly for the expert in the art that although the state of the art and the problem on which the invention is based is disclosed with detail with reference to perfusion, the technique according to the prior art and thus also the technique according to the present invention may be applied without need of further inventive activity and only by means of the basic knowledge of the expert in the art for representing the tissue properties measured by means of other physical parameters of the ultrasound echoes reflected by the tissue.

The above-disclosed known methods can give information of tissue properties related to certain parameters only by comparing the parameters which are pure numerical data. Since the information achieved is related to only one segment, the method must be repeated for each segment. Furthermore, it is difficult to clearly recognize and remember to which region of the object, such as the myocardial wall, the calculated parameters come from; therefore, no direct and immediate comparison is possible.

BRIEF SUMMARY OF THE INVENTION

An object of the present invention is to provide an enhanced method for imaging the parameters of a tissue relating to a certain tissue property using the method according to the prior art as disclosed above and allowing at the same time to build an image in which the parameter value of each pixel or group of pixels is represented by a certain kind of appearance of the pixel or of the group of pixels and in which each pixel or group of pixels is represented in a pixel array in the correct or approximately correct spatial relation to the other pixels or groups of pixels as their spatial relation exists in the real object.

The present invention achieves the above-mentioned aims by means of a method for generating time independent images of moving objects with the image information being related to properties of the moving object represented by providing a sequence of two- or three-dimensional digital images of an object in motion.

The image information of the image sequence is transformed into a series of space-time representations of the image data, such as the value of a variable affecting the pixel appearance for each pixel or group of pixels positioned on a series of adjacent line-segments, so called "transmural cuts", which line-segments are positioned in such a way as to cross the moving object or the moving part of the object and are distributed in such a way as to cover the entire moving object or the entire moving part of the object.

Each space-time image of each transmural cut related to different images of the sequence is aligned in order to compensate for the motion of the object along the transmural cuts by translating and/or scaling each image along the same transmural cut at certain times relative to the other images taken at other times of the image sequence, in order to shift the images of the sequence along the same transmural cut which are taken at different times essentially for a distance corresponding to the displacement of the moving object or of the moving part of the object at the transmural cut and at a corresponding time.

An evaluation function is defined, having at least one parameter, and calculating for each pixel or group of pixels the value of the parameter for best fit of the evaluation function with the curve representing the values of the pixel or group of pixels as a function of time obtained from the aligned space time images.

A parametric image is constructed by defining a pixel appearance scale univocally or uniquely correlated to the parameter value obtained by the best fitting of the evaluation function and by giving to each pixel or group of pixels along each transmural cut a pixel appearance related to the corresponding calculated value of the parameter.

In particular, the present invention provides for a method of acquiring a sequence of a certain number of digital images of a region of interest of an object which has at least one part performing a cyclic or oscillatory or non-oscillatory motion.

At least one segment of a line is defined to be moving, oriented in such a way as to cross the part of the object and having a starting and ending point which lie outside the image of the part of the moving object.

A certain number of pixels or groups of pixels is defined along that segment line and an image is generated for each of the pixels along the segment-line and each of the images are printed or visualized together side by side in the correct time sequence, thus forming a two dimensional image defined by two axes where one axis is the distance along the line-segment, i.e. the position of each pixel or group of pixels along the said line-segment, and the other axis is time.

The motion of the part of the object is compensated by aligning relative to time the single adjacent images of the pixels or group of pixels along the line-segment being taken at different times by shifting and/or stretching relative to the distance axis the position of the pixels or group of pixels along the line for each image along the line-segment taken at different times.

The pixel data, such as brightness or the like, obtained from the digital image of each pixel or group of pixels along the line-segment is retrieved and represents the pixel data in a two-dimensional image defined by two axes where one axis is the pixel data, such as brightness, and the other axis is time.

An estimation function of the pixel data, such as the brightness, is defined as the function of time having at least one parameter.

The parameters of the estimation function leading to the best fit of the estimation function with the time dependent data obtained from the images are calculated.

A certain number of further line-segments are defined and placed side by side in order to cover at least a certain zone of the part of the object performing the cyclic or oscillatory or non-oscillatory motion.

The preceding steps are repeated for each pixel or group of pixels along each of the further line segments.

A scale of pixel appearance is defined which is univocally or uniquely related to the values of at least one parameter and which defines different appearances of the pixels or group of pixels.

An image is reconstructed in which each pixel is positioned on its segment-line in its corresponding position, and the segment-lines are correctly positioned one with respect to the other and in which each pixel has a pixel appearance corresponding to the value calculated for at least one parameter of the pixel or group of pixels.

According to the method of the invention, it is possible to evaluate the appropriate parameter or parameters for each pixel of the sequence of digital images such as, for example, an echographic loop, and it is possible to build new images with the graphic representation of such parameters.

This kind of imaging is defined in the present specification as parametric imaging and is the synthesis of a sequence of digital images such as, but not limited to, an echographic loop, into a few parametric images where a parametric image is a representation of a parametric quantity, or a mathematical parameter, extracted from the analysis pixel by pixel, or of group of pixels, of the evolution of a moving tissue property.

Parametric imaging can be extended to moving objects, such as tissues or any other kind of objects, of which digital images have been taken with any kind of imaging method. Particularly relevant in medicine is the parametric imaging applied to the myocardium. The digital images may be acquired as echographic images or as Nuclear Magnetic Resonance (NMR) images. A first difficulty comes from the fact that each pixel does not correspond (often not even approximately) to the same tissue region during the physiological motion and is overcome by the method according to the present invention which, with the pixel alignment step, also allows separation of the time component by giving an image of the moving object or of a part of the moving object frozen relative to time.

The method according to the present invention allows continuous tracking in time not only of parts of an object which perform motions inside a two-dimensional digital image, but also inside three-dimensional representations (images or volume data sets). This is well suited for the case when the myocardium wall is relatively thin. After the wall is recognized, it is straightforward to analyze the time evolution of properties in correspondence to the detected wall.

The pixel values considered can be the brightness of a black and white image or one or more of the variables of a color image.

The alignment of the images along a segment-line at different times to freeze the motion of an imaged moving object can be carried out according to several methods known from the art. As a first example, statistical algorithms can be used. Another way is to use contour recognition algorithms. Still another way of aligning the images along the same segment line taken at different times is to determine the barycentre of the image along each line and to calculate shift parameters of each line relative to the distance axis.

As an estimation function to be fitted with the data obtained from the images, i.e. the pixel value or values such as brightness, hue, saturation, or color, it is suggested from literature of tissue perfusion to use an exponential function of the form $y(t)=A(1-e^{-Bt})$, where $y(t)$ is the pixel value depending on time, t is the time at which the pixel value was obtained in the image, and A and B are two parameters. Using such a function, the two parameters can be determined for the best fitting function.

The parameters can be imaged into different images built according to the parametric imaging method of the present invention, with both able to be imaged into a two-dimensional or three-dimensional image.

The value scale for imaging the different values of the parameters A and or B can be a color scale, which relates different colors to different pixel values or which relates different brightness or saturation values to a unique color for different pixel values.

Reconstructing the image according to the above-disclosed method would lead to an image comprising pixels only along each of the different line-segments distributed over the image area of the object and being at a certain distance one from the other.

According to a further embodiment, interpolation algorithms can be used to define pixel values for the pixel of the image lying between two adjacent line-segments by considering the pixel values along each of the two adjacent line-segments. So instead of reconstructing a partial image, the entire pixel array or image area can be used for imaging the parameters.

Considering that the parametric image has to be used in order to carry out comparisons with the parametric images of other objects, parametric imaging allows the carrying out of a simple visual analysis by comparing images and also the quantitative comparison of numerical data in a pixel, a group of pixels, or a specific region of interest.

DETAILED DESCRIPTION OF THE PREFERRED EMBODIMENTS

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

Various aspects of the invention are novel, nonobvious, and provide various advantages. While the actual nature of the invention covered herein can only be determined with reference to the claims appended hereto, certain forms and features, which are characteristic of the preferred embodiments disclosed herein, are described briefly as follows.

Further objects, features, aspects, forms, advantages and benefits shall become apparent from the description and drawings contained herein.

Figure 1:
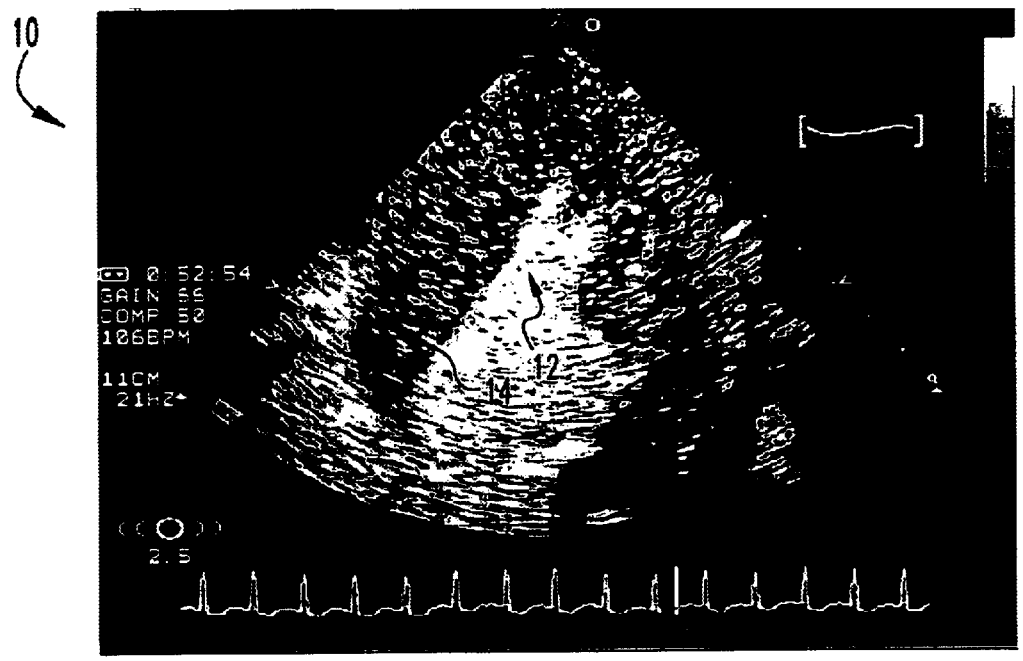
FIG. 1 is an example of an echographic image of the myocardium.

Referring now to the figures, FIG. 1 illustrates a digital image 10 obtained by echographic imaging of a heart 12. The myocardium wall 14 can be clearly seen.

Figure 2:
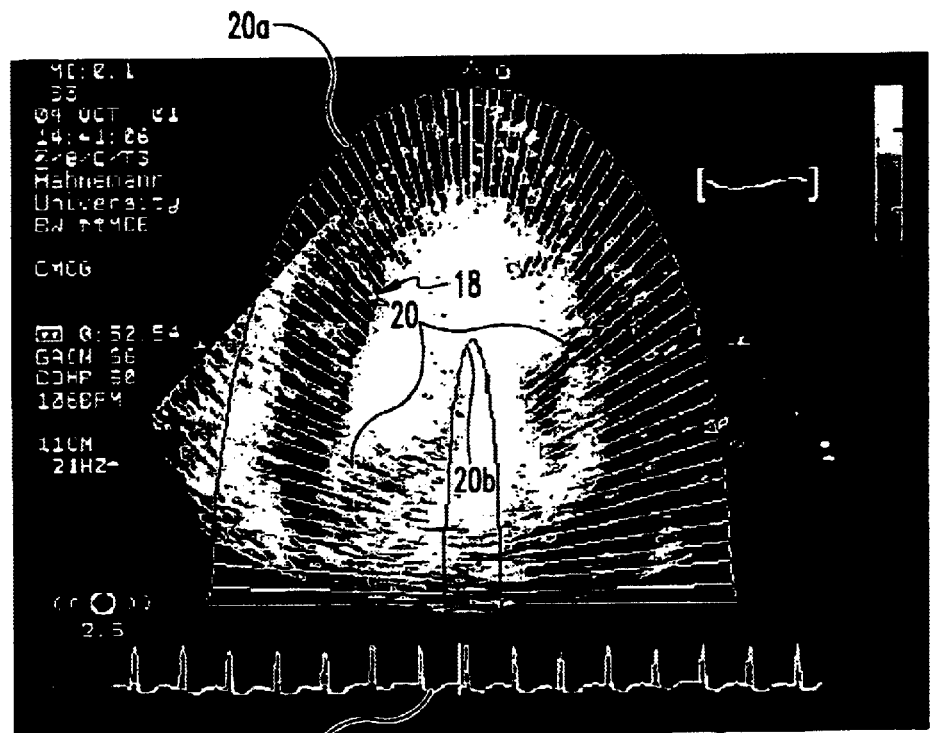
FIG. 2 is an echographic image of the myocardium on which a series of transmural cuts has been superimposed.

FIG. 2 illustrates an echographic image 16 of the myocardium 18 on which a series of adjacent so-called transmural cuts 20, i.e. line segments, are superimposed on the image of myocardium 18. Transmural cuts 20 are distributed over the image area representing myocardium 18 at certain distances one from the other, preferably but not necessarily at constant distances one from the other and in such a way as to cover the entire area of myocardium 18 which is the relevant interesting object in this example.

Each transmural cut 20 has a length and is positioned in such a way that its origin 20a and its end 20b lie outside the outer wall 30 and inner wall 32 of myocardium 18 and have such a distance from it as to be sure that due to movements of myocardium 18 during the heart cycle, the myocardium 18 wall does not fall outside each transmural cut.

As a first step of the method according to the present invention, a certain number of images or frames are taken at different successive times in order to have a time dependent image sequence.

There is no limit to the number of images in the sequence due to the fact that the method leads to results with a small error and that the method does not take much calculation or imaging time to be carried out. This applies also for the number of transmural cuts 20 which are distributed over the area of the region of interest as illustrated in FIG. 2.

Figure 3:
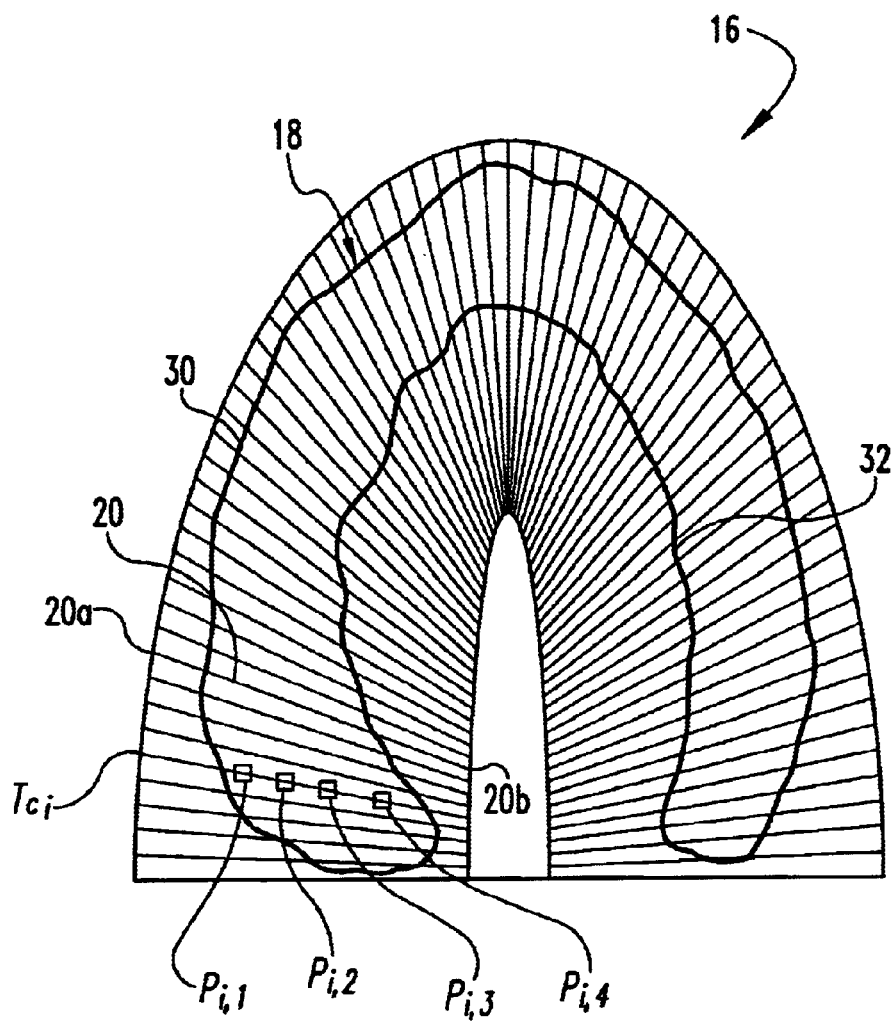
FIG. 3 is a schematic drawing representing the image according to FIG. 2, in which a series of transmural cuts has been indicated.

In order to have a more precise idea of the steps of the method according to the invention, the image of FIG. 2 has been represented in a schematic way with a drawing which is illustrated in FIG. 3.

In FIG. 3, the transmural cut $TC_i$ is the i-th transmural cut of the different and adjacent transmural cuts of the series.

For each of the transmural cuts 20, a sequence of images will be acquired and registered. In FIGS. 1 and 2, the ECG signals 22 and 24 of the heart are represented under the echographic images 10 and 16, respectively.

Along each transmural cut 20, a certain number of pixels are selected. Also, this selection is taken according to the needs of the precision of the image. It depends merely on the resolution which is wanted in the final image. In the example of the schematic drawings of FIGS. 3, 6, 7 and 11, the pixels have been chosen far away from each other in order to better appreciate the way of working of the method. This situation does normally not correspond to the real situation where the pixels are more closely spaced one to the other. Furthermore, it has to be noted that depending on the property which is examined, it might be useful to consider groups of pixels instead of single pixels, so the definition "pixel" is always to be intended as comprising also the term "group of pixels".

In the example of FIG. 3, a specific transmural cut $TC_i$ is illustrated along which the pixels $P_{i,1}$ to $P_{i,4}$ have been illustratively shown in order to better explain the method according to the present invention.

It is to be further noted that although the figures are directed to an example considering echographic images of a biological object such as a heart, the method according to the present invention can be applied to any kind of digital image of any kind of moving object which has properties capable of being described by parameters.

Furthermore, the present example is directed to the evaluation of the perfusion of contrast agents in the myocardium as a means for providing information on the perfusion of blood. Thus each pixel has a different brightness with different concentrations of the contrast agent in the tissue of the myocardium, i.e. in the blood micro-vessels of the myocardium.

This concentration varies with time, and the position of the pixels $P_{i,1}$ to $P_{i,4}$ varies with time due to the alternating motion of myocardium 18 which is caused by the heart cyclic contraction motion.

The transmural cuts $TC_i$ have a length which is chosen to be sufficient for the moving myocardium to always appear inside the length of each transmural cut.

Figure 4:
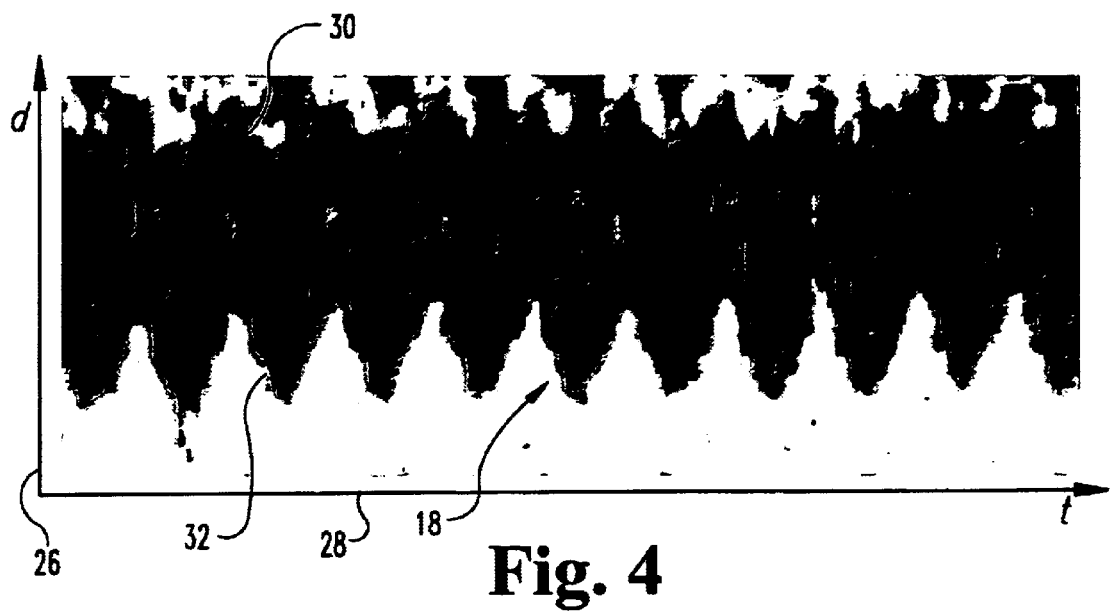
FIG. 4 illustrates an image representing the space-time dependence of the image along one transmural cut.

FIG. 4 represents an image where the image data taken along a certain transmural cut, in this case transmural cuts $TC_i$, is taken at different times and is positioned one beside the other in the correct time sequence. Due to the oscillating or cyclic motion of the myocardium, the space-time diagram has upper and lower approximately sinusoidal edges. The vertical axis 26 represents the position d of the pixels along the transmural cut as taken from the origin of the transmural cut, while the horizontal axis 28 represents time t.

Figure 6:
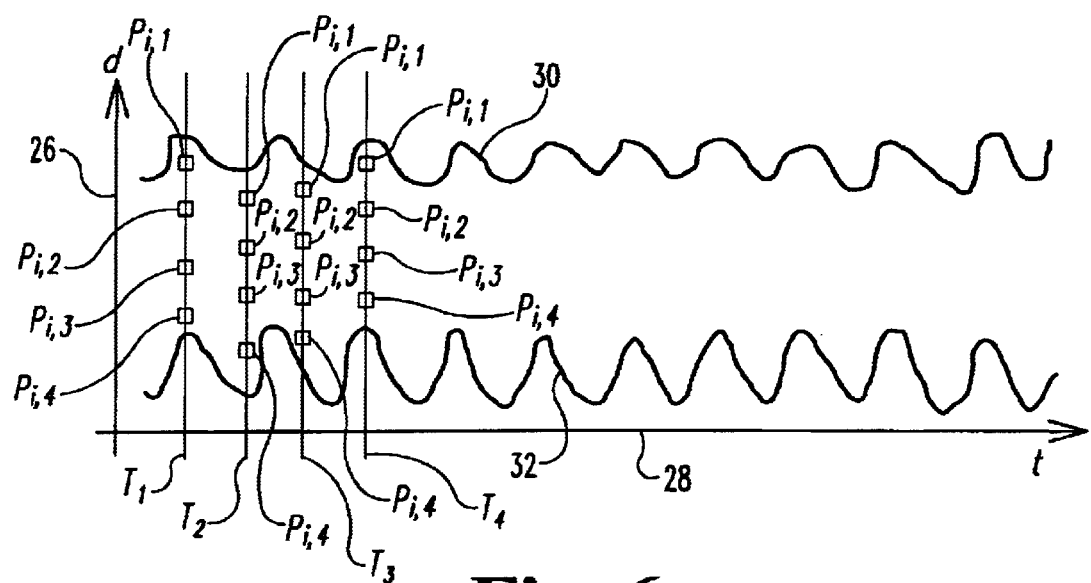
FIGS. 6 and 7 are schematic diagrams representing the images of FIGS. 4 and 5, in which four selected pixels $P_{i,1}$ to $P_{i,4}$ along the transmural cut are illustrated at four different times.

FIG. 6 is a drawing simplifying the image of FIG. 4 and bringing it into relation with the four pixels $P_{i,1}$ to $P_{i,4}$ shown in FIG. 3. The position of the pixels is illustrated with reference to four different times T1 to T4, which are chosen spaced one from the other for better understanding purposes.

As it is shown in FIG. 6, due to the movement of the myocardium, the pixels $P_{i,1}$ to $P_{i,4}$ related to the same points or zones of the myocardium along a transmural cut have at each time T1 to T4 a different position as computed from the origin of the transmural cut.

The sequence of images along the transmural cut has a double time dependence. One dependence is related to the changing of the perfusion of contrast agent in the myocardium, which affects the brightness of the pixels, and the other dependence is due to the motion of the myocardium.

In order to eliminate the second time dependence, the method according to the present invention carries out an alignment step with respect to the time of the single pixel images. In this case, the step will produce a vertical shift of the pixel images at the different times which will align each of the four different pixels related to an image at a certain time with the corresponding pixel on each other image occurring at different times. This operation or step must be carried out by considering that the myocardium has a shape with a cross section which is not constant. Any kind of edge recognition algorithm or method commonly known in image processing may be used for determining the correct edges of the myocardium. Statistical algorithms might also be used for carrying out the alignment which amounts to calculating the value of the vertical shift of the pixels at the different times T1 to T4. Another solution calculates the vertical shift parameter for each pixel at different times by using a barycentre function of the undulated image of FIGS. 4 and 6 and determining the shift in such a way as to maintain the straight barycentre line in the middle of the cross section of the myocardium between the two opposite edges.

Figure 5:
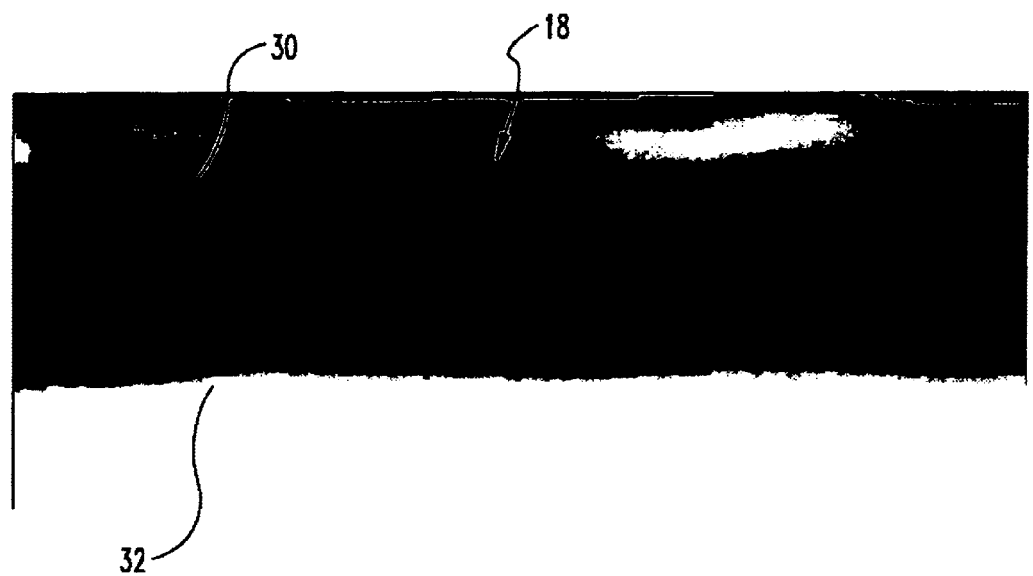
FIG. 5 illustrates the image according to FIG. 4, after alignment, in which motion of the myocardium is frozen.
Figure 7:
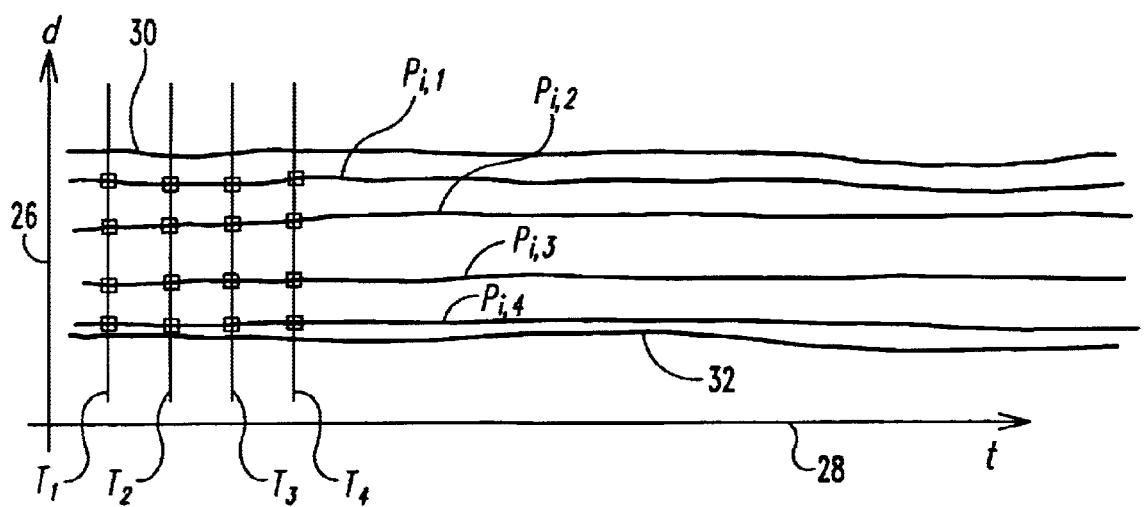

The result of this operation is illustrated in the image of FIG. 5, which is a real image of an example, and in the drawing of FIG. 7, which relates to the simplified schematic diagram of FIG. 6.

The time-dependent space image obtained for each transmural cut is shown as a frozen image of the myocardium with respect to its motion, but which still contains the time dependence of the brightness values of the pixels.

Figure 8:
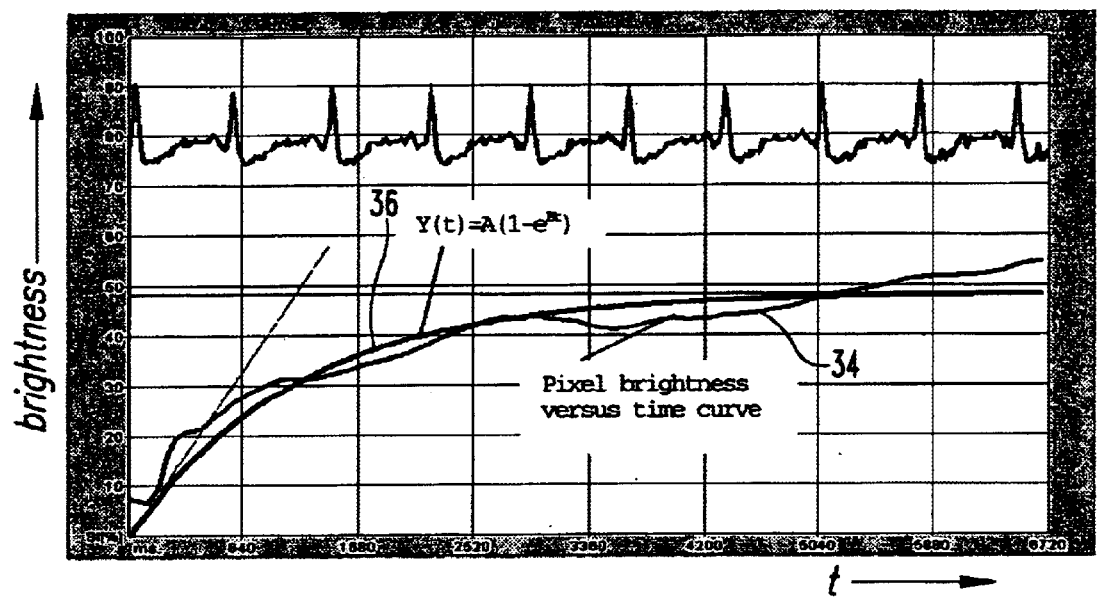
FIG. 8 illustrates a diagram representing the relation between the brightness of one group of pixels in the images of FIGS. 4 and 5 relative to time and the best fit curve of an estimation function.

For each pixel, it is now possible to draw a brightness time function, which is illustrated for the present example as line 34 in FIG. 8. In this case, the time dependence of the brightness of the pixels on the transmural cut $TC_i$ have been plotted or represented. According to a further step, for each pixel $P_{i,k}$ of each transmural cut $TC_1$, the said above-mentioned steps are carried out, and furthermore for each pixel $P_{i,k}$ of each transmural cut $TC_1$, the parameters of an estimation function giving the best fit of the estimation function with the time dependence curve of the pixel brightness is calculated.

Typically this estimation function is an exponential function, such as, for example, the function used for fitting the brightness time curve due to contrast agent perfusion, which is a function of the kind $y(t)=A(1-e^{-Bt})$, where y(t) is the brightness and t is the time. The curve obtained by the best fit of this function with the brightness time curve of FIG. 8 is also illustrated as line 36 in FIG. 8.

Parameters A and B are calculated to define the best fitting function. The computation of parameters A and B can be carried out by means of conventional and long-time known non-linear error minimization algorithms such as the least square error minimization by the simplex method or the like.

These parameters A and B give a time independent measure of the perfusion properties of the myocardium at the corresponding pixel. By carrying out this parameter computation step for each pixel of each transmural cut, there are obtained a certain number of pixels $P_{i,k}$ having a defined position relative to one another and having a univocally or uniquely related pair of best fit parameters $A_{i,k}$ and $B_{i,k}$. The position is precisely defined by the position of the transmural cut $TC_i$ in the pixel array of the image and by the position of the pixels $P_{i,k}$ on the transmural cut $TC_i$.

The computed value of the parameters $A_{i,k}$ and $B_{i,k}$ for each pixel $P_{i,k}$ can be brought into a univocal or unique relationship with a pixel value corresponding to a scale of different pixel appearances. For example, this scale might consider a certain frequency range with definite frequency steps based on the color of the pixels, which vary with the variation of the value of the parameters. Another way of rendering visible the parameter value is to chose for each parameter a certain color and defining a step-like or continuous brightness scale of that color which is related uniquely to the parameter value. Any kind of combination of the variables commonly used for defining the pixel appearance in a digital image formed by an array of pixels may be used in order to create a pixel appearance scale uniquely related to the parameter values.

As a last step of the method of the present invention, an image is reconstructed by printing or visualizing each pixel $P_{i,k}$ along each transmural cut $TC_i$ in the corresponding position of a pixel array, that is in the position as defined by the position of the transmural cut $TC_i$ and by the position of the pixel $P_{i,k}$ along the corresponding transmural cut, and by giving to each pixel $P_{i,k}$ an appearance relating to its values, for example color, brightness, or any kind of appearance defined by any kind of combination of variables defining pixel appearance which are uniquely related to the value of the parameter $A_{i,k}$ and/or $B_{i,k}$ of the related pixel $P_{i,k}$.

Figure 10:
FIG. 10 is a three-dimensional image generated according to the present invention analogous to the image of FIG. 9, for a second parameter.
Figure 9:
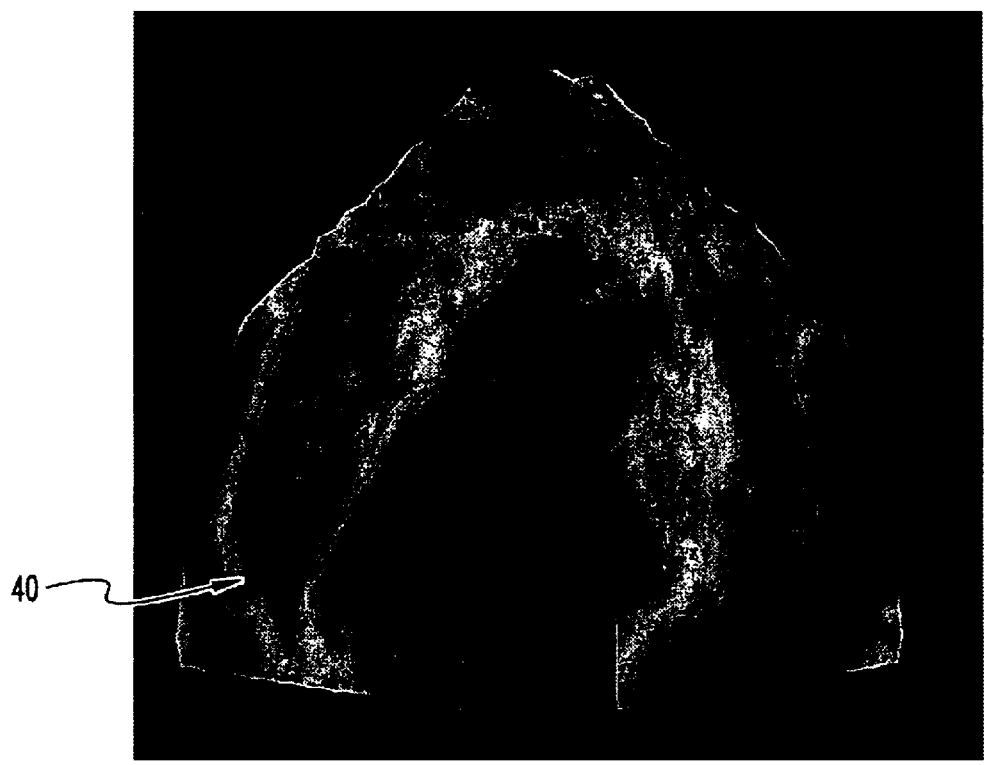
FIG. 9 illustrates an image generated according to the present invention, in which the value of each pixel along each of the transmural cuts represents the value of one of the parameters of the best fit curve by means of a univocal pixel appearance scale.

An example of the result of this last step is illustrated for the parameter $A_{i,k}$ in the two-dimensional image of a myocardium 40 shown in FIG. 9 and for the parameter $B_{i,k}$ in the three-dimensional image of a myocardium 42 shown in FIG. 10.

Figure 11:
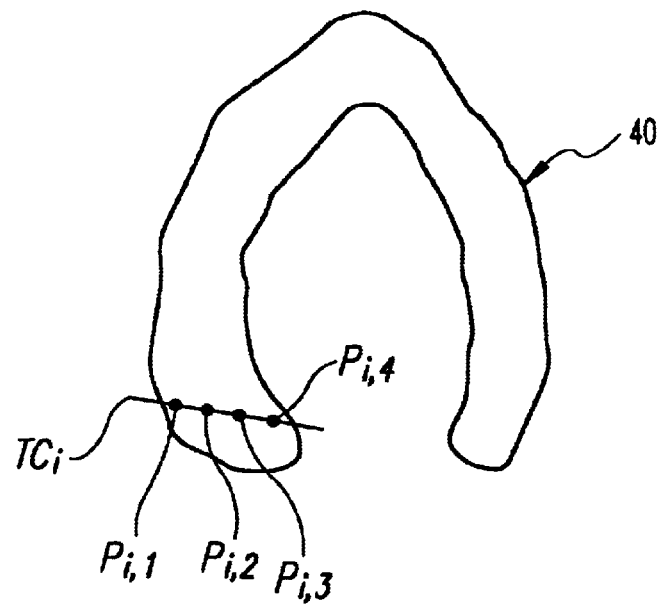
FIG. 11 is a schematic representation of the image according to FIG. 9, an appearance corresponding to the calculated parametric values correlated to the parametric value of the pixels.

FIG. 11 is a drawing which shows the construction of the image illustrated in FIG. 9 by means of a simplified example.

It can be appreciated in all the three FIGS. 9, 10, and 11 that giving to the pixels $P_{i,1}$, $P_{i,2}$, $P_{i,3}$, and $P_{i,4}$ a position as defined by the corresponding transmural cut $TC_i$ and by the position of the pixel on the transmural cut $TC_i$, an image of the myocardium can be constructed in which each pixel has an appearance which is univocally or uniquely related to the value of the parameter $A_{i,k}$ and/or $B_{i,k}$ calculated for each pixel. This allows, in an embodiment of the present invention, direct comparison of the perfusion properties of the myocardium in different patients and/or with different tissues.

It is further noted that the average position of the pixels on the corresponding transmural cut can be calculated with the alignment step described above, so the image of the myocardium obtained relative to its shape is frozen and time independent.

Alternatively, the position of the pixels $P_{i,k}$ on the corresponding transmural cuts $TC_i$ can be determined in one of the sequence of echographic images, so that the image of the myocardium obtained relative to its shape has at a certain time of acquisition a certain echographic image of the sequence.

Furthermore, it has to be noted that the term "echographic image" does not refer exclusively to an echographic image but also to an image frame. The sequence of echographic images can also be interpreted as a sequence of image frames. This is important since often echographic images are obtained by acquisition of a certain number of frames which are then combined to form a single image. In the case of a moving object which is to be imaged, it is preferable to use as a sequence of images a sequence of image frames.

FIG. 10 shows the same result as FIGS. 9 and 11 but includes the second parameter B and uses a three-dimensional representation in order to show that a parametric image may also be interpreted to be a three-dimensional function associating a parameter value with a space position. In fact, the method of the present invention associates numerical, quantitative parameter values to each pixel that are commonly best visualized in color-scale images, but which can also be represented in different ways.

The present invention contemplates modifications as would occur to those skilled in the art. It is also contemplated that processes embodied in the present invention can be altered, rearranged, substituted, deleted, duplicated, combined, or added to other processes as would occur to those skilled in the art without departing from the spirit of the present invention. In addition, the various stages, steps, procedures, techniques, phases, and operations within these processes may be altered, rearranged, substituted, deleted, duplicated, or combined as would occur to those skilled in the art. All publications, patents, and patent applications cited in this specification are herein incorporated by reference as if each individual publication, patent, or patent application was specifically and individually indicated to be incorporated by reference and set forth in its entirety herein.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. A method for generating time independent images of moving objects comprising the following steps:

providing a sequence of digital images of the moving part of an object;

transforming image information of said sequence into a series of space-time images comprised of pixels or groups of pixels on a series of adjacent line-segments, said line-segments being positioned in such a way as to cross the said moving part of said object and being distributed in such a way as to completely cover said moving part of the said object;

aligning said space-time images of each of said line-segments related to different images of said sequence in order to compensate for motion of said moving part of said object along said line-segments by shifting said images of said sequence taken at different times along a given line-segment for a distance corresponding to the displacement of said moving part of said object;

defining an evaluation function having at least one parameter and calculating for each pixel or group of pixels the value of the said parameter for best fitting said evaluation function with a curve representing the values of said pixel or group of pixels obtained from said aligned space-time images; and constructing a time independent image of said moving object by defining a pixel appearance scale univocally correlated to said at least one parameter and using said evaluation function.

2. The method according to claim 1 characterised in that the pixel values comprise the brightness of a black and white digital image or one or more of variables of a color image.

3. The method according claim 1 characterised in that said alignment of said images along said segment at different times for freezing said motion of said object is carried out in accordance with a statistical algorithm.

4. The method according to claim 1, characterised in that said alignment of said images along said segment at different times for freezing said motion of said object is carried out by means of edge or contour recognition algorithms.

5. The method according to claim 1, characterised in that said alignment of said images along said segment at different times for freezing said motion of said object is carried out by determining the barycentre line between upper and lower edges of said image along each of said segments and calculating parameters of each of said segments relative to the distance of said pixels on said segment from an origin.

6. The method according to claim 1, characterised in that said estimation function is of the form $y(t)=A(1-e^{-Bt})$, where $y(t)$ is the pixel value depending from time, t is the time at which the pixel value has been determined in the image and A and B are parameters giving the best fit of said estimation function.

7. The method of claim 6, characterised in that said parameters can be imaged in a two-dimensional or a three-dimensional image, or in any known representation of a function of one, two, or more variables.

8. The method according claim 6, characterised in that said pixel appearance scale for imaging different values of said is a color scale.

9. The method according to claim 1, characterised in that an interpolation algorithm is used for defining pixel values for pixels lying between two adjacent segments by interpolating the pixel values along each of said two adjacent segments.

10. The method according to claim 1, characterised in that said image sequences are formed by echographic images.

11. The method according to claim 1, characterised in that said image sequence is formed by MRI images.

12. The method according to claim 1, characterised in that said image sequence is formed by images acquired by analogic acquisition methods.

13. The method according to claim 12, wherein said analogic acquisition methods comprise photographic and radiographic methods.

14. The method according to claim 1, characterised in that said pixel data comprises the brightness of said pixels of said image sequence.

15. The method according to claim 1, characterised in that said pixel data is obtained by imaging modes comprising Doppler, power Doppler, B-mode, and Harmonic imaging.

16. The method according to claim 1, characterised in that said moving object is the myocardium of the heart.

17. The method according to claim 1, characterised in that said pixel data is related to the presence of a contrast agent in the tissue of the myocardium.

18. The method according to claim 1, characterised in that said pixel data is a measurement of the contrast agent perfusion in a biologic tissue.

19. A method for generating time-independent images of moving objects, comprising the steps:

acquiring a sequence of a plurality of digital images of a region of interest of an object which has at least one part performing a cyclic or oscillatory or non oscillatory motion;

defining at least one segment of a line oriented in such a way as to cross the moving part of said object, said segment having a starting point and ending point which lie outside said images of said moving part of said object;

defining a certain number of pixels or groups of pixels along said segment;

generating a first image of each pixel or group of pixels along said segment such that a plurality of images are presented in the correct time sequence so as to form a two-dimensional image defined by two axes, where one axis is the distance position of each pixel or group of pixels along said segment and the other axis is time;

compensating the motion of said moving part of said object by aligning relative to time adjacent images of said pixels or group of pixels along said segment by shifting relative to the distance axis said position of said pixels or group of pixels along said segment for at least part of each image along said segment taken at different times;

retrieving pixel data from said digital image of each of said pixels or groups of pixels along said segment and representing said pixel data in a two-dimensional image defined by two axes, where one axis is said pixel data and the other axis is time;

defining an estimation function of said pixel data as a function of time, where said function has at least one parameter;

calculating said parameter of said estimation function leading to the best fit of said estimation function with said pixel data;

defining a plurality of additional segments which are placed side by side in order to cover at least a portion of said moving part of said object;

repeating said preceding steps with respect to each pixel or group of pixels along each of said additional segments;

defining a scale of pixel appearance which is univocally related to the values of said at least one parameter and which defines different appearances of said pixels or groups of pixels; and reconstructing an image representative of said moving part of said object in which each of said pixels or groups of pixels is positioned on a segment in a time-independent position and where each of said pixels or groups of pixels has an appearance corresponding to the value calculated for said at least one parameter with respect to said pixel or group of pixels.

20. The method according to claim 19, characterised in that said pixel data comprises the brightness of a black and white digital image or one or more of variables of a color image.

21. The method according claim 19, characterised in that said compensation of said motion is carried out in accordance with a statistical algorithm.

22. The method according to claim 19, characterised in that said compensation of said motion is carried out by means of edge or contour recognition algorithms.

23. The method according to claim 19, characterised in that said compensation of said motion is carried out by determining the barycentre line between upper and lower edges of said image along each of said segments and calculating parameters of each of said segments relative to the distance of said pixels on said segment from an origin.

24. The method according to claim 19, characterised in that said estimation function is of the form $y(t)=A(1-e^{-Bt})$, where y(t) is the pixel value depending from time, t is the time at which the pixel value has been determined in the image and A and B are parameters giving the best fit of said estimation function.

25. The method of claim 24, characterised in that said parameters can be imaged in a two-dimensional or a three-dimensional image, or in any known representation of a function of one, two, or more variables.

26. The method according claim 24, characterised in that said pixel appearance scale for imaging different values of said is a color scale.

27. The method according to claim 19, characterised in that an interpolation algorithm is used for defining pixel values for pixels lying between two adjacent segments by interpolating the pixel values along each of said two adjacent segments.

28. The method according to claim 19, characterised in that said image sequences are formed by echographic images.

29. The method according to claim 19, characterised in that said image sequence is formed by MRI images.

30. The method according to claim 19, characterised in that said image sequence is formed by images acquired by analogic acquisition methods.

31. The method according to claim 30, wherein said analogic acquisition methods comprise photographic and radiographic methods.

32. The method according to claim 19, characterised in that said pixel data comprises the brightness of said pixels of said image sequence.

33. The method according to claim 19, characterised in that said pixel data is obtained by imaging modes comprising Doppler, power Doppler, B-mode, and Harmonic imaging.

34. The method according to claim 19, characterised in that said moving object is the myocardium of the heart.

35. The method according to claim 19, characterised in that said pixel data is related to the presence of a contrast agent in the tissue of the myocardium.

36. The method according to claim 19, characterised in that said pixel data is a measurement of the contrast agent perfusion in a biologic tissue.

* * * * *